604-270 SR
10/15/85 OR 4,547,192

United States Patent [19]
Brodsky et al.
[11] Patent Number: 4,547,192
[45] Date of Patent: Oct. 15, 1985

[54] GASTROENTERIC FEEDING TUBE

[75] Inventors: David L. Brodsky, Providence; Harry O. Olsen, Jr., Warwick, both of R.I.

[73] Assignee: Superior Plastic Products Corp., Cumberland, R.I.

[21] Appl. No.: 484,413

[22] Filed: Apr. 11, 1983

Related U.S. Application Data

[63] Continuation-in-part of Ser. No. 441,362, Nov. 12, 1982, abandoned.

[51] Int. Cl.[4] .......... A61M 1/00
[52] U.S. Cl. .......... 604/270; 604/282
[58] Field of Search .......... 604/270, 280, 282, 48, 604/73, 93; 128/207.14

[56] References Cited

U.S. PATENT DOCUMENTS

| | | | |
|---|---|---|---|
| 243,396 | 6/1981 | Pfarre | 604/282 |
| 1,736,182 | 11/1929 | Wilkens | 604/270 |
| 2,583,298 | 1/1952 | Kowan | 604/282 |
| 3,618,613 | 11/1971 | Schulte | 604/282 |
| 4,044,765 | 8/1977 | Kline | 604/282 X |
| 4,390,017 | 6/1983 | Harrison et al. | 604/270 |
| 4,410,320 | 10/1983 | Dykstra et al. | 604/270 |

FOREIGN PATENT DOCUMENTS

| | | | |
|---|---|---|---|
| 1216482 | 5/1966 | Fed. Rep. of Germany | 604/270 |

*Primary Examiner*—Stephen C. Pellegrino
*Attorney, Agent, or Firm*—Salter & Michaelson

[57] ABSTRACT

A gastroenteric feeding tube for the enteral feeding of hospital patients includes a resiliently flexible coil spring as a weighting element. The coil spring which is encased within a flexible casing provides a flexible weighting element which can be installed in and removed from a patient with a minimum of discomfort. Once the feeding tube has been properly installed in the patient, the weighting element end thereof can safely remain in the patient's stomach for an extended period of time without substantial risks. In one embodiment of the feeding tube, a flexible tubular member extends axially through the coil spring weighting element thereof. Hence, a continuous longitudinal passage is provided in the feeding tube which allows the accurate installation of the tube in the gastrointestinal tract of a patient with the aid of a pre-installed guide wire or stylet.

4 Claims, 7 Drawing Figures

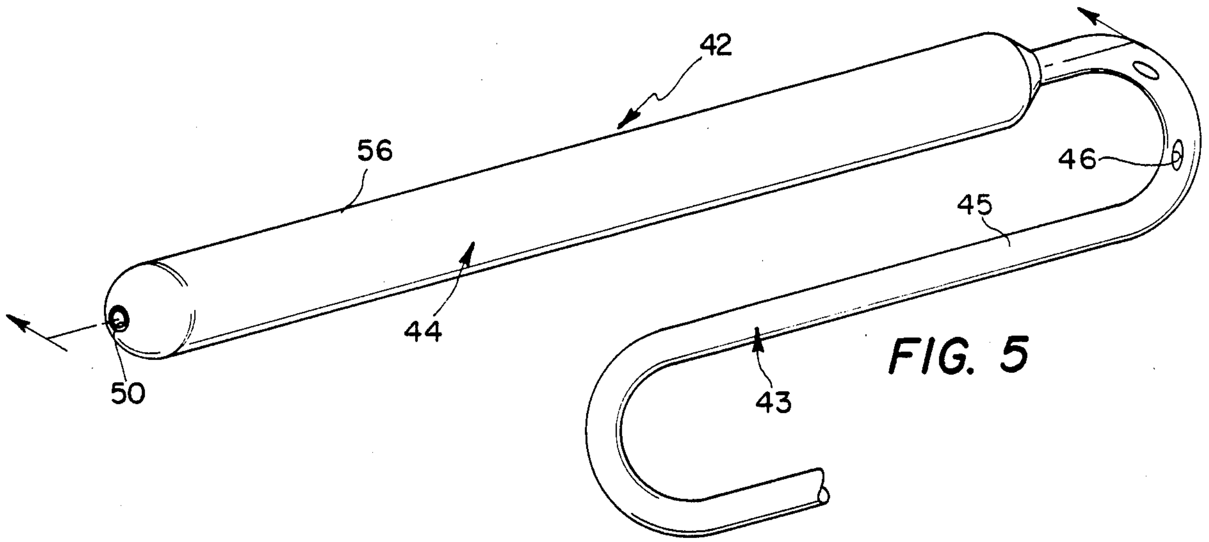
FIG. 5
FIG. 6
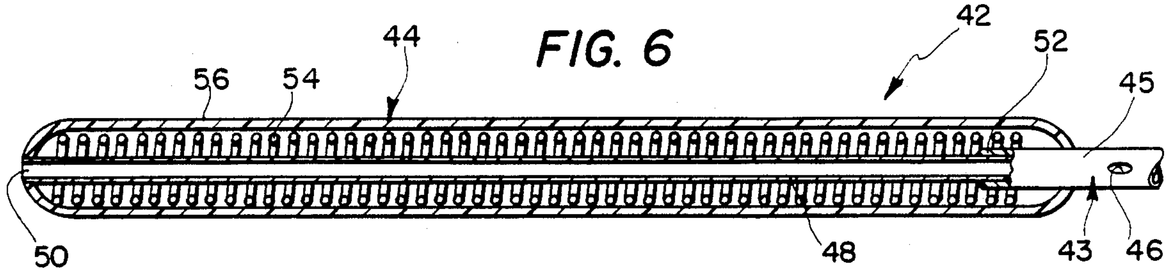
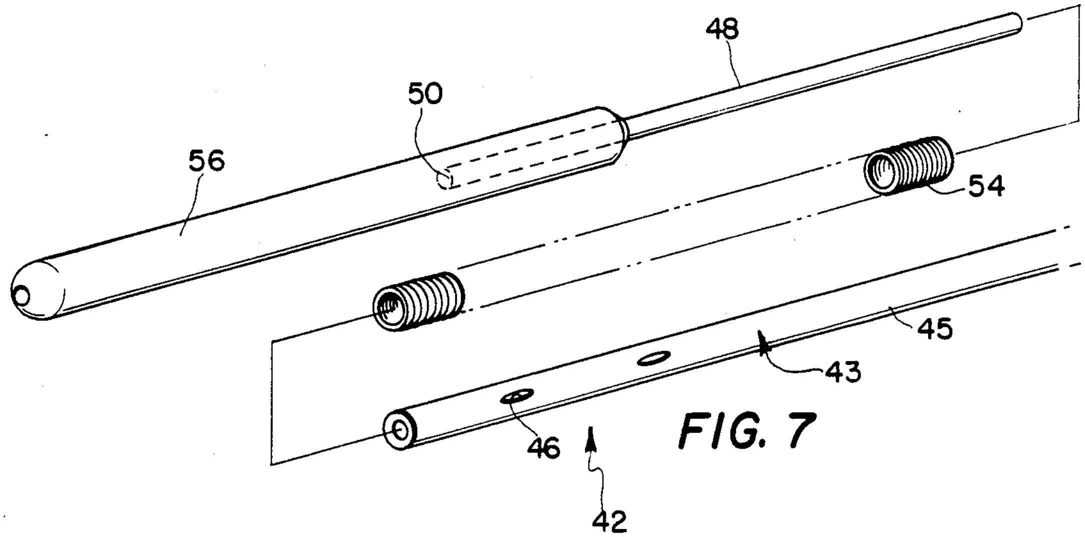
FIG. 7

GASTROENTERIC FEEDING TUBE

BACKGROUND AND SUMMARY OF THE INVENTION

This application is a continuation-in-part of application Ser. No. 441,362, filed on Nov. 12, 1982 now abandoned.

The instant invention relates to the artificial feeding of hospital patients, and more particularly to the enteral feeding of such patients by tube.

The use of gastroenteric or, as sometimes called nasoenteric feeding tubes, for the enteral feeding of patients is widely accepted in medical practice. Feeding tubes of this type are most commonly used when a patient is unable to meet his or her nutrional requirements through oral intake, but nevertheless has a functional gastrointestinal tract. In such instances, enteral feeding has frequently proven to be preferable to parenteral feeding for both medical and nutritional reasons. When a tube of this type is to be used to feed a patient, it is installed so that it extends through the patient's nostril, through the esophagus, into the stomach and sometimes into the patient's intestines. Once a gastroenteric feeding tube has been properly installed in a patient, it can frequently remain therein for continual or repeated usage over a prolonged period of time which may exceed a month or more. However, it has been found that when prolonged artificial feeding is required, it is essential that a gastroenteric tube be installed in the patient so that it extends past the patient's pyloric valve and into the patient's intestines. When a feeding tube has been installed in this manner it can provide effective feeding of the patient for a prolonged period and the malnutrition and weight loss effects sometimes associated with other types of artificial feeding devices can be avoided.

The most common heretofore known gastroenteric feeding tube constructions have comprised an elongated flexible tubular member which is preferably made of a silicon rubber and which has at least one aperture adjacent an end thereof and a weighting element which is secured to the tubular member adjacent the apertured end. When the feeding tube is installed in a patient, feeding of the patient can be effected through the tubular member so that the feeding formula passes through the aperture and into the patient's stomach or intestines. The use of a weighting element on the lower end of the tubular member has proven to be necessary, particularly where the lower end of the tube is disposed in the patient's stomach, in order to avoid complete or partial expulsion of the feeding tube as a result of regurgitation. In this connection, while a weighting element must be of sufficient weight to prevent such expulsion, it must be embodied in a flexible configuration which permits the insertion thereof through a patient's nostril during installation of the feeding tube. One widely used type of heretofore known feeding tube construction includes a quantity of mercury contained within a flexible tubular casing on the lower end of the tube to provide a weighting element. However, while a mercury weighting element is flexible and can provide sufficient weight to maintain the lower end of a feeding tube in a patient's stomach, the risks associated with the possibility of introducing mercury into a patient's system are apparent. Another type of heretofore known feeding tube construction includes a plurality of aligned metallic balls which are contained within a flexible tubular casing on the lower end of the tube to provide a weighting element. This type of weighting element can also provide sufficient weight to maintain the lower end of a tube in a patient's stomach, but in some instances it may not be sufficiently flexible and hence may result in patient discomfort both during and after installation. Further, the use of this type of weighting element also presents certain risks relative to the possible release of foreign materials into the patient's stomach.

As hereinabove mentioned, when prolonged feeding of a patient is required, it is essential that a feeding tube be installed so that the lower portion thereof extends past the patient's pyloric valve and into the intestines. The heretofore known procedure for installing tubes in this manner has relied on the natural operation of the patient's stomach to carry the lower end of the tube past the pyloric valve and into the intestines. Specifically, the heretofore known procedure has required that a tube be installed so that the lower end thereof and a certain amount of excess tubing is received in the patient's stomach, whereby the natural movement of the patient's stomach hopefully carries the lower end of the tube past the patient's pyloric valve and into the intestines. Unfortunately, it has been found that this method only works approximately 75% of the time and, therefore, in a number of cases the lower end of the tube never gets past the patient's pyloric valve. Consequently, in instances where prolonged feeding is required and the above described method has failed to provide proper tube installation, surgical intervention has been necessary whereby the lower end of a feeding tube is manually installed into a patient's intestinal track. In this regard, while the disadvantages of surgery are apparent, in many instances this has been the only effective method of properly installing a feeding tube in a patient so that proper feeding of the patient can be assured.

The instant invention provides a novel solution to the problem of providing an effective and safe flexible weighting element for a gastroenteric feeding tube and also provides a novel solution to the problem of installing a feeding tube in a patient's stomach so that the tube extends past the patient's pyloric valve and into the intestines. Specifically, the feeding tube of the instant invention comprises an elongated flexible tubular member having an aperture adjacent an end thereof, a resiliently flexible coil spring weighting element, and means encasing the weighting element and securing it in substantially aligned relation on the apertured end of the tubular member. The coil spring, which is preferably made of either tungsten or steel, is resiliently flexible to minimize patient discomfort both during and after the installation of the feeding tube. Further, the coil spring provides sufficient weight on the apertured end of the tubular member to maintain said end in the patient's stomach. The use of a coil spring weighting element also eliminates the above described hazards associated with other types of weighting elements, and in fact, even if the casing of a coil spring weighting element were to rupture, there would be no release of hazardous foreign materials, such as mercury or metallic balls, into the patient's stomach. In the preferred embodiment of the instant invention, the tubular member actually extends in substantially coaxial relation through the coil spring weighting element and has an open terminal end, whereby a continuous open passage is provided which extends through the entire length of the feeding tube.

When the feeding tube is embodied in this configuration, it can be accurately installed in a patient's stomach so that it extends past the patient's pyloric valve and into the intestines. Specifically, since the tube has an axial opening which extends completely therethrough it can be installed over a guide wire which has been properly positioned in the patient's stomach. In this regard, the use of controllable guide wires or "stylets" which can be accurately guided through various portions of a patient's body is well known in the medical profession. Accordingly, by positioning a patient in front of a fluoroscope so that the movement of a guide wire in the patient can be observed, it is possible to install the wire so that it extends into the patient's stomach, past the pyloric valve, and into the patient's intestines. Thereafter, by inserting the upper end of the guide wire into the feeding tube, the tube can be passed along the guide wire, whereby the wire is used to guide the installation of the feeding tube to assure that it extends into the patient's stomach, past the pyloric valve, and into the patient's intestine area.

The closest prior art to the instant invention of which the applicant is aware is disclosed in the U.S. patents to Stratton et al., U.S. Pat. No. 3,395,710; Shermeta, U.S. Pat. No. 3,915,171; Smith, U.S. Pat. No. 4,182,342; and Hargest, III, U.S. Pat. No. 4,249,535. While the above patents teach the use of tungsten powder and mercury as weighting elements in feeding tube constructions, they do not teach or suggest the use of a coil spring for a weighting element and they also do not teach a feeding tube having an axial opening or passage which extends therethrough, and hence the cited references are felt to be of nothing more than general interest.

Accordingly, it is a primary object of the instant invention to provide an effective and safe gastroenteric feeding tube.

Another object of the instant invention is to provide a gastroenteric feeding tube which utilizes a coil spring as a weighting element.

Another object of the instant invention is to provide a gastroenteric feeding tube which can be effectively and reliably installed so that the lower portion of the tube extends into a patient's intestinal tract.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 5 is a perspective view of the weighting element end portion of an alternate embodiment of the feeding tube of the instant invention;

FIG. 6 is a sectional view taken along line 6—6 in FIG. 5; and

FIG. 7 is an exploded perspective view of the weighting element end portion illustrated in FIG. 5.

DESCRIPTION OF THE INVENTION

Figure 1:
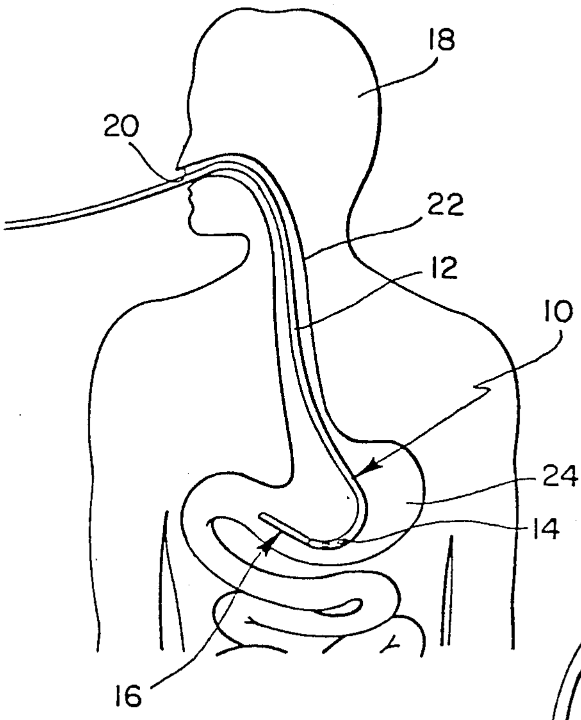
FIG. 1 is a schematic view of a person with a gastroenteric feeding tube installed therein.
Figure 2:
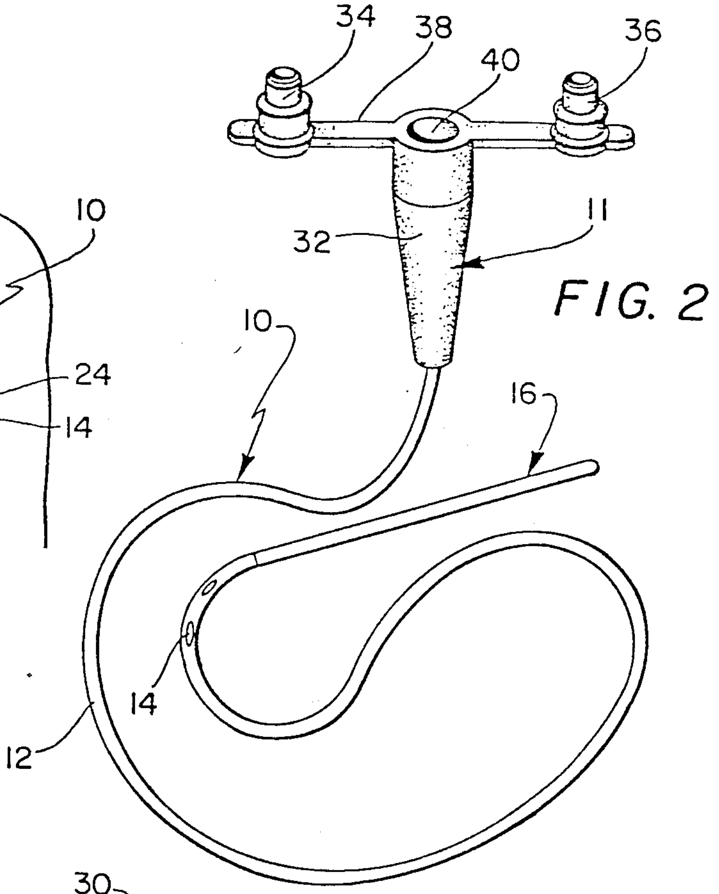
FIG. 2 is a perspective view of the feeding tube with a plug adapter mounted on the upper end thereof.

Referring now to the drawing, particularly FIGS. 1 and 2, a first embodiment of the gastroenteric feeding tube of the instant invention is illustrated and generally indicated at 10. The feeding tube 10, which is illustrated in FIG. 2 in combination with a plug adapter 11, generally comprises an elongated flexible tubular member 12 having at least one aperture 14 therein adjacent the lower end thereof and a weighted lower terminal portion generally indicated at 16 which is attached to the apertured end of the member 12. As illustrated in FIG. 1, the feeding tube 10 is installed in a patient 18 so that it extends through a nostril 20, through the esophagus 22, and into the stomach 24 of the patient 18. When so installed, the terminal portion 16 provides a weight at the lower end of the tubular member 12 to maintain said end in the stomach 24. Accordingly, fluid communication may be provided between an external feeding source and the stomach 24 by means of the tubular member 12, the fluid passing through the apertures 14 therein and into the stomach 24.

The tubular member 12 comprises an elongated flexible element which is preferably constructed of a suitable inert, flexible, nontoxic rubberized material, such as silicone rubber.

Figure 3:
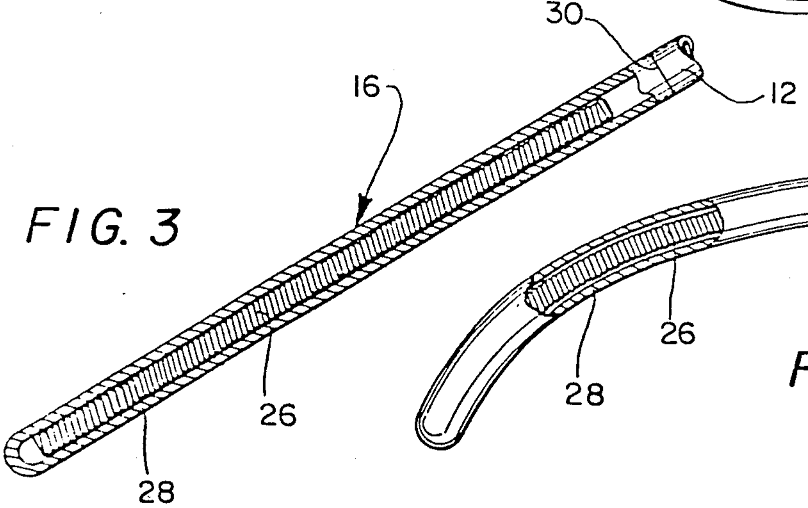
FIG. 3 is an enlarged sectional view of the weighting element end of the feeding tube.
Figure 4:
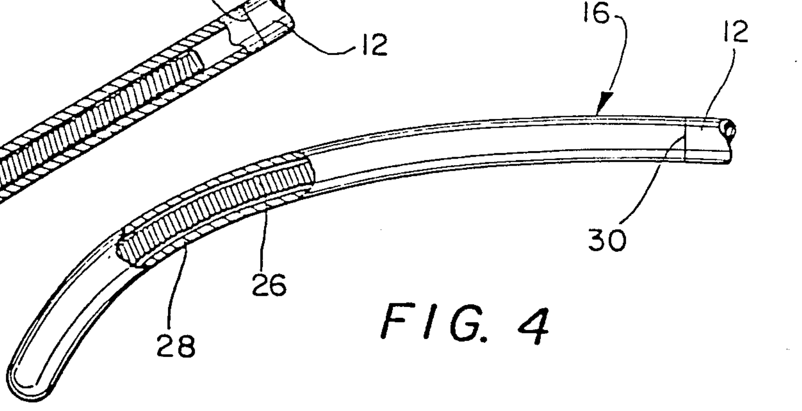
FIG. 4 is an enlarged view thereof in partial section illustrating the weighting element in a flexed disposition.

The terminal portion 16, which is illustrated most clearly in FIGS. 3 and 4, comprises an elongated resiliently flexible coil spring 26 which is preferably made of steel or tungsten, and a flexible casing 28 which completely encases the spring 26. In this regard, it will be understood that the spring 26 preferably has sufficient flexibility so that it will easily bend to minimize patient discomfort during the installation and removal of the feeding tube 10. The casing 28 is also preferably made of a suitable inert, flexible, nontoxic rubberized material such as silicone rubber, and is secured to the lower end of the tubular member 12 by a suitable adhesive or by fusing as at 30. It will be understood, however, that other embodiments of the instant invention wherein the casing 28 is integrally formed on the lower end of the tubular member 12 are contemplated. In any event, as illustrated in FIG. 4, the important point is that the coil spring 26 provides a weighting element which is safe and which is resiliently flexible to minimize patient discomfort during the installation and removal of the feeding tube 10. In the feeding tube 10, the coil spring 26 is of slightly smaller diameter than the tubular member 12 and the casing 28 is of substantially the same diameter as the tubular member 12 so that the terminal portion 16 and the tubular member 12 are flush so as to easily pass through a patient's nostril to further minimize patient discomfort during the installation and removal of the feeding tube 10.

The plug adapter 11, which does not in itself comprise part of the instant invention, is secured to the upper end of the tubular member 12 to receive a feeding formula therein from an external source. In this connection, the plug adapter 11 comprises a socket portion 32, a reducer member 34, the plug member 36, and a flexible connector piece 38 which integrally connects both the reducer member 34 and the plug member 36 to the socket member 32. The passing 40 extends through the socket member 32 to receive a feeding formula in the tubular member 12 and the reducer member 34 and the plug member 36 are alternatively receivable in the passage 40 to alternatively provide a reduced opening therefor or a closure member therefor, respectively.

A second embodiment of the feeding tube of the instant invention is illustrated in FIGS. 5-7 and generally indicated at 42. The feeding tube 42 comprises an elongated flexible tubular member 43 and a resiliently flexible weighted bolus portion 44 which is secured to the lower end of the member 43. The tubular member 43 includes a main portion 45 having a plurality of apertures 46 therein, and a reduced terminal portion 48 which terminates in an opened terminal end 50. The reduced terminal portion 48 is received in the main portion 45 and is secured thereto by suitable means such as an adhesive or by fusing as at 52. The main portion 45 and the terminal portion 48 are preferably both made of a suitable inert, flexible, nontoxic rubberized material such as silicone rubber, and they cooperate to define a continuous elongated open passage in the tubular member 43 which terminates in the open end 50. The bolus portion 44 comprises a resiliently flexible coil spring 54 which is preferably made of tungsten or steel, and an outer casing 56 which is preferably made of a suitable inert, flexible, nontoxic rubberized material such as silicone rubber. The coil spring 54 is received on the reduced terminal portion 48 so that the terminal portion 48 extends substantially axially therethrough. As a result, the interior of the tubular member 43 communicates with the exterior of the feeding tube 42 through the longitudinal interior passage defined by the coil spring 54. The casing 56 is sealed at the ends thereof to the tubular member 43 and encases the coil spring 54. Accordingly, the spring 54 and the casing 56 cooperate to define a resiliently flexible weighting element on the lower end of the tubular member 43. However, since the reduced terminal portion 48 extends through the bolus portion 44, an axial passage is provided which extends through the entire length of the feeding tube 42.

The feeding tube 42 is particularly adapted for installation in a patient utilizing a guide wire or guide stylet. Specifically, a guide wire or stylet of the type widely used in the medical profession which is accurately guidable or directable in a patient's gastrointestinal tract with the aid of a fluoroscope is installed in the patient, preferably so that the terminal portion of the wire or stylet extends past the patient's pyloric valve and into the intestinal track. The feeding tube 42 is then received on the upper end of the wire or stylet so that the wire or stylet extends into the tubular member 43 and the tube 42 is advanced along the wire and into the patient. As the feeding tube is further advanced into the patient, the wire functions as a guide, whereby the bolus portion 44 is directed past the patient's pyloric valve and into the patient's intestinal track. After the tube 43 has been properly installed, the guide wire is withdrawn to provide an open tube for feeding the patient. Accordingly, it is seen that by providing a feeding tube 42 having a passage which extends axially therethrough, the feeding tube 42 can be installed in a patient so that the lower portion of the feeding tube 42 extends past the patient's pyloric valve whereby the bolus portion 44 and the portion of the tubular member 43 adjacent thereto is received in the patient's intestinal track. In this connection, for the first time it is possible to install the feeding tube 42 so that it is received in a patient in this manner without depending on the frequently unreliable natural action of the patient's stomach or on surgical intervention. When the tube 42 has been installed in a patient in this manner, feeding of the patient can be effected through the apertures 46 as well as through the end 50. However, if the end portion of the tube 42 should become bent or crimped, so that feeding formula can no longer reach the end 50, feeding can nevertheless be continued through the apertures 46.

It is seen, therefore, that the instant invention provides an effective feeding tube which can be used for the gastroenteric feeding of patients with maximum patient safety and minimum patient discomfort. In this connection, both the coil springs 26 and 54 in the feeding tubes 10 and 42, respectively, provide sufficient weight to maintain the lower ends of the respective tubes in the stomachs of patients, but the springs are inherently safer for this purpose than the weighting elements such as mercury and metallic balls utilized in the heretofore known enteric feeding devices. Further, the flexibility and configurations of the weighting elements 26 and 54 provide for minimum patient discomfort during installation and removal of the feeding tubes 10 and 42. The feeding tube 42 also provides the advantage that it can be installed in a patient so that the lower portion of the tube extends through the patient's pyloric valve and the bolus portion 44 is received in the patient's intestines. Hence, it is seen that the instant invention represents a significant advancement in the art which has substantial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A gastroenteric feeding tube comprising:

a. an elongated flexible tubular member;

b. a resiliently flexible coil spring weighting elements; and c. means encasing said weighting element and securing it in substantially aligned relation on an end of said tubular member, said tubular member extending substantially coaxially through said weighting element and having an open terminal end, whereby a continuous open longitudinal passage is provided in said feeding tube.

2. In the feeding tube of claim 1, said weighting element being made of steel.

3. In the feeding tube of claim 1, said weighting element being made of tungsten.

4. In the feeding tube of claim 1, said weighting element further characterized as being of slightly smaller diameter than said tubular member, said encasing means further characterized as being of substantially the same diameter as said tubular member.

* * * * *